United States Patent
Dafni et al.

(10) Patent No.: US 6,914,957 B2
(45) Date of Patent: Jul. 5, 2005

(54) WIRELESS DATA TRANSMISSION IN CT-SCANNERS

(75) Inventors: Ehud Dafni, Caesaria (IL); James W. Green, South Russell, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 262 days.

(21) Appl. No.: 10/312,952

(22) PCT Filed: Dec. 19, 2001

(86) PCT No.: PCT/US01/49152

§ 371 (c)(1),
(2), (4) Date: Dec. 27, 2002

(87) PCT Pub. No.: WO03/053246

PCT Pub. Date: Jul. 3, 2003

(65) Prior Publication Data

US 2003/0185338 A1 Oct. 2, 2003

(51) Int. Cl.[7] ............................................... A61B 6/00
(52) U.S. Cl. ............................................ 378/15; 378/4
(58) Field of Search ............................. 378/4, 15, 901; 375/130, 146, 147, 259, 295, 316

(56) References Cited

U.S. PATENT DOCUMENTS

| | | | |
|---|---|---|---|
| 4,641,317 A | 2/1987 | Fullerton | 375/130 |
| 4,813,057 A | 3/1989 | Fullerton | 375/259 |
| 4,979,186 A | 12/1990 | Fullerton | 375/259 |
| 5,140,696 A | 8/1992 | Fox | 455/41.1 |
| 5,363,108 A | 11/1994 | Fullerton | 342/27 |
| 5,469,488 A | 11/1995 | Ono | 378/15 |
| 5,530,422 A | 6/1996 | Harrison | 340/500 |
| 5,530,424 A | 6/1996 | Harrison | 340/500 |
| 5,530,425 A | 6/1996 | Harrison | 340/500 |
| 5,537,397 A | 7/1996 | Abramson | 370/441 |
| 5,577,026 A | 11/1996 | Gordon et al. | 370/278 |
| 5,978,438 A | 11/1999 | Resnick et al. | 378/4 |
| 6,031,862 A | 2/2000 | Fullerton | 375/146 |
| 6,181,766 B1 * | 1/2001 | Pearson et al. | 378/15 |
| 6,301,324 B1 * | 10/2001 | Pearson et al. | 378/15 |
| 6,754,297 B2 * | 6/2004 | James | 378/4 |

FOREIGN PATENT DOCUMENTS

DE        195 33 820        3/1996

OTHER PUBLICATIONS

Schilling, D.L.; Pickholtz, R.L.; Milstein, L.B.;"Spread Spectrum Goes Commerical" Spectrum, IEEE ,vol.: 27 , Issue: 8 , Aug. 1990 pp.: 40–41, 44–45.*

* cited by examiner

Primary Examiner—David V. Bruce
Assistant Examiner—Courtney Thomas
(74) Attorney, Agent, or Firm—Thomas M. Lundin

(57) ABSTRACT

A CT-scanner having a gantry comprising a stator and a rotor, wherein an X-ray source and array of X-ray detectors are mounted to the rotor for determining absorption of X-rays along paths through the body of a patient imaged by the CT-scanner, the CT imager comprising: a processor that processes data comprised in signals generated by the X-ray detectors responsive to intensity of X-rays from the X-ray source incident on the detectors to generate an image of the patient; at least one spread spectrum transmitter that receives data comprised in the signals generated by the X-ray detectors and transmits signals encoded with the data in accordance with a spread spectrum coding; and at least one spread spectrum receiver that receives the encoded signals transmitted by the at least one spread spectrum transmitter and forwards the encoded data to the processor.

28 Claims, 1 Drawing Sheet

WIRELESS DATA TRANSMISSION IN CT-SCANNERS

RELATED APPLICATIONS

This application is a U.S. national filing of PCT Application No. PCT/US01/49152, filed on Dec. 19, 2001.

FIELD OF THE INVENTION

The present invention relates to computerized tomography (CT) X-ray imaging, and in particular to methods to methods and apparatus for transmitting data generated by X-ray detectors in a CT-scanner to a processor that generates and displays images responsive to the data.

BACKGROUND OF THE INVENTION

In CT X-ray imaging of a patient, X-rays are used to image internal structure and features of a region of the person's body. The imaging is performed by a CT-imaging system, hereinafter referred to as a "CT-scanner" that images internal structure and features of a plurality of contiguous relatively thin planar slices of the body region using X-rays.

The CT-scanner generally comprises an X-ray source that provides a planar, fan-shaped X-ray beam and an array of closely spaced X-ray detectors that are coplanar with the fan beam and face the X-ray source. The X-ray source and array of detectors are mounted in a gantry so that a person being imaged with the CT-scanner, generally lying on an appropriate support couch, can be positioned within the gantry between the X-ray source and the array of detectors. The gantry and couch are moveable relative to each other so that the X-ray source and detector array can be positioned axially at desired locations along the patient's body.

The gantry comprises a stationary structure referred to as a stator and a rotary element, referred to as a rotor, which is mounted to the stator so that the rotor is rotatable about the axial direction. In third generation CT-scanners the X-ray source and detectors are mounted to the rotor. Angular position of the rotor about the axial direction is controllable so that the X-ray source can be positioned at desired angles, referred to as "view angles", around the patient's body.

To image a slice in a region of a patient's body, the X-ray source is positioned at the axial position of the slice and the X-ray source is rotated around the slice to illuminate the slice with X-rays from a plurality of different view angles. At each view angle, detectors in the array of detectors measure intensity of X-rays from the source that pass through the slice. The intensity of X-rays measured by a particular detector in the array of detectors is a function of an amount by which X-rays are attenuated by material in the slice along a path length from the X-ray source, through the particular slice, to the detector. The measurement provides information on composition and density of tissue in the slice along the path-length.

For example, let incident X-ray intensity sensed by an "n-th" detector in the array of detectors when the X-ray source is located at a view angle $\theta$ is represented by $I(n,\theta)$, then $I(n,\theta)=I_O\exp(-\int\mu(l)dl)$. In the expression for $I(n,\theta)$, $I_O$ is intensity of X-rays with which the X-ray source illuminates the slice, integration over l represents integration over a path through material in the slice along a direction from the X-ray source to the n-th detector and $\mu(l)$ is an absorption coefficient for X-rays per unit path-length in the material at position l along the path. (Dependence of the integral on n and $\theta$ is not shown explicitly and is determined through dependence of the length and direction of the path-length l on n and $\theta$.)

From $I_O$ and the sensed $I(n,\theta)$, an amount by which X-rays are attenuated along path-length l and a value for the integral $\int\mu(l)dl$, hereinafter referred to as an "line integral", can be determined. The attenuation measurement provided by the n-th detector at the view angle $\theta$ therefore provides a value for the line integral of the absorption coefficient along a particular path length through the slice which is determined by $\theta$ and the known position of the n-th detector relative to the X-ray source.

The set of attenuation measurements for a slice provided by all the detectors in the detector array at a particular view angle $\theta$ is referred to as a view. The set of attenuation measurements from all the views of the slice is referred to as a "projection" of the slice. Values for the line integral provided by data from the projection of the slice are processed using algorithms known in the art to provide a map of the absorption coefficient $\mu$ as a function of position in the slice. Maps of the absorption coefficient for the plurality of contiguous slices in the region of the patient's body are used to display and identify internal organs and features of the region.

In some CT-scanners, to image a region of a patient, a sequential scan of the patient is performed in which the region is scanned by moving the patient stepwise in the z direction to "step" the region through the gantry that houses the X-ray source and detector array. Following each step, the X-ray source is rotated through 360 degrees or $(180+\Delta)$ degrees, where $\Delta$ is an angular width of the fan beam provided by the X-ray source, to acquire a projection of a slice of the region. In some CT-imagers a "spiral scan" of a patient is performed in which the region of the patient is steadily advanced through the gantry while the X-ray source simultaneously rotates around the patient and projections of slices in the region are acquired "on the fly". In some CT-scanners, referred to as multislice CT-scanners, a plurality of slices of a region of a patient are simultaneously imaged. Often as many as four slices of a region of a patient are simultaneously imaged by a multislice CT-scanner.

In third generation CT-scanners the X-ray source and the detectors are mounted on the imager's rotor. Data generated by the detectors responsive to intensity of X-rays incident on the detectors has to be transferred from the rotor to a location of a processor that generates images from the data and displays the generated images.

Many different methods and systems are available for transmitting data generated by detectors on the rotor of a CT-scanner to a desired location for processing and display. However, the immediate environment of the rotor is generally electromagnetically very noisy. As a result, free space transmission of the data using electromagnetic waves has not been considered practical. Usually, data generated by the detectors is transferred from the rotor over very short distances to the stator via contact connections or non-contact "proximity" connections between the rotor and stator. From the stator the data is transmitted via wire or optical fiber to a desired location where the data is processed and/or displayed.

In some third generation CT-scanners electromechanical, contact slip-rings provide contact connections between the imager's rotor and stator for transmitting data from the rotor to the stator. However, present day CT-scanners generate data at data rates between 20–800 Mbits/s and data rates are increasing as CT-scanners become faster and multislice CT-scanners acquire projections of an increasing plurality of slices simultaneously. Contact slip-rings generally cannot support reliable data transfer at data transfer rates that match rates at which modern third generation CT-scanner generate data.

Usually therefore, in modern CT-scanners data is transmitted between the rotor and stator via non-contact proximity links, which links may, for example, be optical or electromagnetic. Various types of such non-contact links are commercially available, for example, from Schliefring (Germany), Litton Poly-Scientific (USA) and ElectroTech (USA). However, currently available non-contact links for CT-scanners are generally expensive and they usually complicate mechanical construction of the imagers. Furthermore, present non-contact links generally cannot support data transfer rates about equal to or greater than 1 Gbit/sec.

U.S. Pat. No. 5,577,026 describes a non-contact data link for transferring data between the rotor and stator of a CT-scanner in which the data is transferred via antenna assemblies on the rotor and stator. In an embodiment of the data link the antenna assemblies are capacitively coupled and data is transferred between the antenna using RF signals. The inventors note that IR, UV or optical frequencies may also be used to transfer data. The inventors describe coding data transmitted over the link using an Ethernet protocol and achieving reliable data transfer rates of approximately 10 megabits per second (Mbits/s).

U.S. Pat. No. 5,530,425 describes a system for transmitting data from a CT-scanner rotor to the imager stator using a transmission line mounted on the rotor and a non-contact proximity RF coupler mounted on the stator which is coupled to the transmission line. The inventor notes that the system supports data transmission rates at 150 Mbits/s.

U.S. Pat. No. 5,469,488 describes an optical system for transmitting data between the rotor and stator of a CT-scanner. A plurality of light emitting elements in the system is located on the rotor or stator and transmits optical signals to a light receiving element mounted respectively on the stator or the rotor to transfer data between the stator and rotor.

SUMMARY OF THE INVENTION

An aspect of some embodiments of the present invention relates to providing a method and apparatus for transmitting data generated by X-ray detectors mounted in a rotor of a CT-scanner gantry to a receiver at a desired location, using free space electromagnetic waves.

An aspect of some embodiments of the present invention relates to providing a method and apparatus for transmitting data generated by the X-ray detectors to a receiver that is located at a position removed form the rotor.

An aspect of some embodiments of the present invention relates to providing a method and apparatus for transmitting data from the detectors that supports reliable data transmission at transmission rates equal to or in excess of 1 Gbit/s.

The inventors have realized that data can be reliably transmitted over free space at high data rates from detectors in a rotor of a CT-scanner to a desired location using spread spectrum coding of electromagnetic waves. Spread spectrum transmission is particularly robust and can be used to reliably and accurately transmit data between locations in an electronically noisy environment via free space electromagnetic waves.

In particular, a spread spectrum transmission technique referred to as "time hopping impulse modulation", hereinafter "THIM", can be used to support reliable, simultaneous data transmission from a large number of data sources located in a same localized noisy environment. In THIM transmission a signal is transmitted as a pulse train of very short pulses, referred to as impulses or monopulses. Each monopulse and a next subsequent monopulse in the pulse train are separated by a time period, referred to as pulse repetition intervals (PRI). The PRIs are generally much longer than a duration of a monopulse and may range from hundreds to thousands of times longer than a duration of a monopulse. The PRI between any two consecutive monopulses is regularly changed in accordance with a predetermined periodic "time hopping code". Data is encoded into the pulse train by making changes in the PRIs, which are additional to those changes made responsive to the time hopping code, that are determined responsive to the data to be encoded. Many THIM transmitters operating in a same neighborhood can usually simultaneously transmit data to a same receiver without data transmitted by one of the transmitters interfering with data transmitted by another of the transmitters. Interference is generally prevented or substantially reduced by operating each of the different transmitters using a different time hopping code.

THIM is described in a series of patents to Fullerton beginning with U.S. Pat. No. 4,641,317, which issued on Feb. 3, 1987, and which was followed by U.S. Pat. Nos. 4,813,057, 4,979,186, and 5,363,108. U.S. Pat. No. 6,031,862, also to Fullerton, notes that theoretical analysis suggests that an RF THIM system can provide thousands of voice channels per cell in a cellular phone system. The disclosures of all the above noted patents to Fullerton are incorporated herein by reference.

In accordance with an embodiment of the present invention, a CT-scanner is provided comprising a data transmission system having at least one THIM transmitter for transmitting data from X-ray detectors mounted on the rotor of the imager to a desired location. In some embodiments of the present invention, the at least one THIM transmitter transmits data from the detectors to a THIM receiver on the gantry stator. Unlike in prior art systems for transmitting data from the rotor to the stator, THIM transmission of data from the rotor to the stator, in accordance with an embodiment of the present invention, does not require that the THIM transmitter and receiver be in physical contact or in close proximity. As a result, use of THIM transmission simplifies construction of the gantry.

In some embodiments of the present invention, the at least one THIM transmitter transmits data from the detectors in the rotor to a receiver located at a distance from the gantry rather than to a receiver on the stator. For example, a receiver may be located in a different part of a same room in which the CT-gantry is located. Since THIM signals can relatively easily be detected after being transmitted through most walls of a building, a receiver may, be in a room different from a room in which the CT-gantry is located. For example, in some embodiments of the present invention a receiver is located at a venue at which the data is processed and/or displayed, which venue may be located in a room different from the room in which the CT-gantry is located.

As noted above, since many THIM transmitters can be operated simultaneously to transmit data, a data transmission system, in accordance with an embodiment of the present invention, can be configured to support a large data transmission rate by providing the system with a sufficient number of THIM transmitters. For example, a THIM transmitter that supports data transmission rates up to about 40 Mbit/sec is currently available from "Time Domain" of Alabama USA in a chipset called "PulsOn. To provide a data transmission system for a CT-system that supports a transmission rate of about 1.2 Mbit/sec the system can be configured to comprise 30 PulsOn chipsets operating in parallel.

In some embodiments of the present invention, data generated by the detectors is preprocessed at the rotor by a suitable processor and the preprocessed data is then transmitted to a receiver by the at least one THIM transmitter. Preprocessing might include for example, in accordance with an embodiment of the present invention, packing the data into data packets having identifying headers and comprising various error correction codes of types known in the art. In some embodiments of the present invention, the headers are used by the receiver to identify data packets that are not received or are corrupted. For missing and/or corrupted data packets the receiver initiates a redundancy protocol in which a missing and/or corrupted packet is retransmitted by the at least one THIM transmitter.

There is therefore provided in accordance with an embodiment of the present invention, A CT-scanner having a gantry comprising a stator and a rotor, wherein an X-ray source and array of X-ray detectors are mounted to the rotor for determining absorption of X-rays along paths through the body of a patient imaged by the CT-scanner, the CT imager comprising: a processor that processes data comprised in signals generated by the X-ray detectors responsive to intensity of X-rays from the X-ray source incident on the detectors to generate an image of the patient; at least one spread spectrum transmitter that receives data comprised in the signals generated by the X-ray detectors and transmits signals encoded with the data in accordance with a spread spectrum coding; and at least one spread spectrum receiver that receives the encoded signals transmitted by the at least one spread spectrum transmitter and forwards the encoded data to the processor.

Optionally, the at least one transmitter comprises at least one time hopping impulse modulation (THIM) transmitter that transmits signals encoded with the data in accordance with a THIM code and the at least one receiver comprises at least one THIM receiver that receives the encoded signals transmitted by the at least one THIM transmitter. Additionally or alternatively, the signals encoded with the data are free space electromagnetic waves encoded with the data.

There is further provided in accordance with an embodiment of the present invention, a CT-scanner having a gantry comprising a stator and a rotor, wherein an X-ray source and array of X-ray detectors are mounted to the rotor for determining absorption of X-rays along paths through the body of a patient imaged by the CT-scanner, the CT imager comprising: a processor that processes data comprised in signals generated by the X-ray detectors responsive to intensity of X-rays from the X-ray source incident on the detectors to generate an image of the patient; at least one transmitter that receives data comprised in the signals generated by the X-ray detectors and transmits free space electromagnetic waves encoded with the data; at least one receiver that receives the encoded free space electromagnetic waves transmitted by the at least one transmitter and forwards the encoded data to the processor.

Optionally, the at least one transmitter comprises at least one spread spectrum transmitter that encodes the data in the free space electromagnetic waves in accordance with a spread spectrum code and the at least one receiver comprises at least one spread spectrum receiver.

Optionally, the at least one transmitter comprises at least one THIM transmitter that encodes the data in the free space electromagnetic waves in accordance with a THIM code and the at least one receiver comprises at least one THIM receiver.

In some embodiments of the present invention, the transmitter and receiver are located in a same room.

In some embodiments of the present invention, the transmitter is located on the gantry and the receiver is at a distance from the gantry. Optionally, the transmitter and receiver are located in different rooms.

In some embodiments of the present invention, the transmitter is located on the stator.

In some embodiments of the present invention, the transmitter is located on the rotor.

In some embodiments of the present invention, the transmitter is located on the rotor and the at least one receiver is located on the stator.

In some embodiments of the present invention, the at least one receiver and the processor are near each other in a same location.

In some embodiments of the present invention, the receiver and the processor are in different rooms.

In some embodiments of the present invention, the at least one receiver is connected to the processor by wire over which the receiver forwards the data to the processor.

In some embodiments of the present invention, the at least one receiver is connected to the processor by optical fiber over which the receiver forwards the data to the processor.

In some embodiments of the present invention, the at least one transmitter comprises a plurality of transmitters. Optionally, the transmitters transmit simultaneously.

Alternatively, or additionally, the at least one receiver comprises a plurality of receivers. Optionally, at least two of the plurality of receivers receives transmissions from different transmitters.

In some embodiments of the present invention, the CT-scanner comprises at least one data acquisition system (DAS) mounted on the rotor connected to the X-ray detectors that receives the signals generated by the X-ray detectors and generates digital data therefrom, portions of which digital data the at least one DAS routes to each of the at least one transmitter. Optionally, the at least one DAS comprises a plurality of DASs each of which acquires signals from different detectors.

There is further provided in accordance with an embodiment of the present invention, a method of transmitting to a desired location data comprised in signals generated by X-ray detectors mounted on a rotor of a gantry comprised in a CT-scanner, the method comprising: generating free space electromagnetic waves encoded with the data; sensing the electromagnetic waves at the desired location; and decoding the sensed electromagnetic wave to recover the data.

Optionally, the data is encoded in accordance with a spread spectrum code. Optionally, the data is encoded in accordance with a time hopping impulse modulation (THIM) code. There is further provided in accordance with an embodiment of the present invention, a method of transmitting to a desired location data comprised in signals generated by X-ray detectors mounted on a rotor of a gantry comprised in a CT-scanner, the method comprising: generating signals encoded with the data in accordance with a spread spectrum code; sensing the signals at the desired location; and decoding the sensed signals to recover the data. Optionally, the code is a THIM code. Additionally or alternatively the signals encoded with the data are free space electromagnetic waves encoded with the data.

BRIEF DESCRIPTION OF FIGURE

Non-limiting examples of embodiments of the present invention are described below with reference to.

DETAILED DESCRIPTION OF EXEMPLARY EMBODIMENTS

Figure 1:
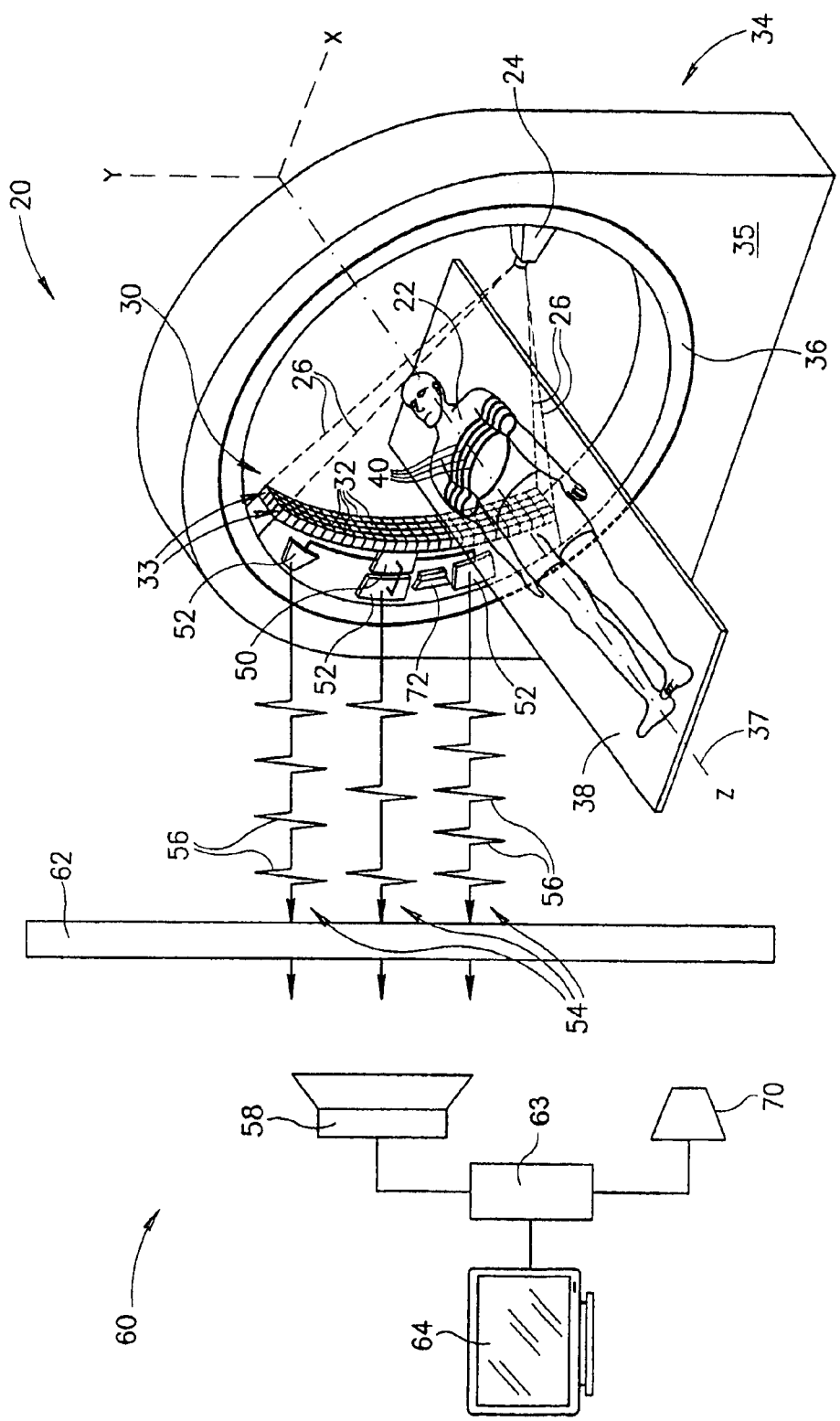
FIG. 1, which schematically shows a CT-scanner having a data transmission system that comprises at least one THIM transmitter, in accordance with an embodiment of the present invention.

FIG. 1 schematically shows a third generation CT-scanner 20 comprising a THIM data transmission system, in accordance with an embodiment of the present invention. In FIG. 1, by way of example CT-scanner 20 is shown imaging a region of the chest of a patient 22. Dimensions of components and features shown in the FIGURE are chosen for convenience and clarity of presentation and are not necessarily shown to scale.

CT-scanner 20 comprises an X-ray source 24 controllable to provide a fan-beam schematically indicated by dashed lines 26 and an array 30 of X-ray detectors 32 mounted opposite the X-ray source for sensing X-rays in the fan-beam. CT-scanner 20 is assumed, by way of example to be a multislice imager that simultaneously images a plurality of four slices of a region of the body of a patient (patient 22 in FIG. 1) being imaged with the CT-scanner. Detectors 32 in array 30 are therefore configured in a plurality of four contiguous curved rows 33 of the detectors. CT-scanner 20 comprises a gantry 34 having a stator 35 to which a rotor 36 is mounted so that the rotor can be controlled to rotate about an axis 37. X-ray source 24 and detector array 30 are fixedly mounted to rotor 36 so that when rotor 36 rotates about axis 37 the X-ray source and detector array also rotate about axis 37.

Patient 22 is supported on a couch 38 during imaging of the patient with CT-system 20. Couch 38 is mounted on a suitable pedestal (not shown) so that couch 38 is controllable to be translated axially along axis 37. Detectors 32 in detector array 30 and features of CT-scanner that are shadowed by patient 22 and couch 38 and would not normally be seen in the perspective of FIG. 1 are shown for clarity of presentation with ghost lines.

For convenience, a coordinate system shown in FIG. 1 having a horizontal x-axis, vertical y-axis and z-axis coincident with axis 37, is used to locate components and features of CT-system 20 and patient 22. The coordinate system is assumed to be fixed with respect to gantry 34. View angle of X-ray source 24 is measured with respect to the y-axis of the coordinate system. Slices of the body of patent 22 are located by the position of the slice along the z-axis.

To image the chest region of patient 22 couch 38 is controlled to translate along the z-axis and move the chest region through the space between X-ray source 24 and detector array 30 to expose the chest region to X-rays and acquire views of slices of the chest region at desired view angles. At each desired view angle detectors 32 in a row 33 of detectors generate signals responsive to intensity of X-rays to which they are exposed that provide a view of a single slice of patient 22. The four rows 33 of detectors 32 generate signals that simultaneously provide views of four different slices of patient 22. In FIG. 1 CT-scanner is shown, by way of example, acquiring views of four slices 40 at a view angle of about 90°.

A data acquisition system (DAS) 50 and, in accordance with an embodiment of the present invention, at least one THIM transmitter 52 are mounted on rotor 36. The signals generated by detectors 32 are transferred by wire (not shown) to a data acquisition system DAS 50 mounted on rotor 36 that processes the signals to generate digital data therefrom. DAS 50 routes, responsive to an appropriate routing algorithm, portions of the digital data that it generates to each of the at least one THIM transmitter 52. Each of the at least one THIM transmitter 52 transmits the data that it receives as "THIM" data signals to an at least one THIM receiver 58 located at a desired venue. THIM signals transmitted by each THIM transmitter 52 are schematically shown as a train 54 of monopulses 56 emitted by the transmitter.

It is noted that whereas in FIG. 1 a single DAS 50 is shown, in some embodiments of the present invention a plurality of DASs is mounted on rotor 36 and that different configurations of the plurality of DASs and the at least one THIM transmitter are possible and can be advantageous. For example, a different DAS of the plurality of DASs may be associated with each row 33 of detectors 32 and each DAS may route digital data that it generates to a different THIM transmitter or transmitters.

By way of example, in FIG. 1 the at least one THIM receiver is a single THIM receiver 58 comprised in a processing station 60 located in a room, which is different from a room in which CT-scanner is located. A "wall" 62 between CT-scanner 20 and processing station 60 schematically indicates that the CT-scanner and processing station may be located in different rooms. Processing station 60 comprises a processor 63 and a visual display console 64 for generating and displaying images of regions of patient 22 from the data it receives from the at least one THIM transmitter 52.

The number of THIM transmitters comprised in CT-scanner 20 is determined to provide sufficient transmission channel capacity to support a data rate at which detectors 32 in detector array 30 generate data. For example, assume that CT-scanner 20 is operated to take views of patient 22 at 2320 views angles per second and that each row 33 of detectors 32 comprises 672 detectors 32. Assume further that DAS 50 converts each signal generated by one of detectors 32 to a 16 bit word. The four rows 33 of detectors 32 comprised in CT-scanner 20 therefore generate data at a rate of about 100 Mbit/sec. Assume that each THIM transmitter 52 supports data transmission rates that are similar to data transmission rates supported by the THIM transmitter provided by the Time Domain chip set PulsOn. Each PulsOn chip set provides a THIM transmitter that supports data transmission rates up to 40 Mbits/sec. At least three THIM transmitters 52, in accordance with an embodiment of the present invention, as shown in FIG. 1, are therefore required to transmit the data generated by CT-scanner 20.

It is noted that a data transmission system for a CT-scanner, in accordance with an embodiment of the present invention, that comprises THIM transmitters is not limited to having a relatively small number of THIM transmitters such as the three THIM transmitters 52 shown in FIG. 1. For example, assume a CT-scanner similar to CT imager 20 that acquires views for sixteen slices simultaneously instead of for four slices and comprises therefore sixteen rows 33 of detectors 32, each having 672 detectors, instead of four rows of the detectors. Assume that the CT-scanner acquires views for 4640 view angles per second and that each signal from a detector 32 in the CT-scanner is converted into a sixteen bit word. The CT-scanner would generate data at a rate of about 800 Mbits/sec. A data transmission system, in accordance with an embodiment of the present invention, for such a CT-scanner would have at least twenty forty-Mbit/sec THIM transmitters 52 of the PulsOn type.

To operate each of THIM transmitters 52 simultaneously and substantially prevent transmission from one THIM transmitter 52 interfering with transmission from another THIM transmitter 52, in some embodiments of the present invention, each THIM transmitter 52 is operated with a different time hopping code. FIG. 1 schematically shows each of THIM transmitters 52 transmitting data to receiver 58 using a different hopping code. The different hopping codes are indicated by a different "temporal" spacings, which schematically represent different PRIs, (i.e. pulse repetition intervals) between monopulses 56 in the different pulse trains 54 emitted by the THIM transmitters 52.

In some embodiments of the present invention, each THIM transmitter 52 operates with a same time hopping code. To separate transmission from different THIM transmitters 52, the transmissions from the different transmitters are temporally offset from each other using a method described in U.S. Pat. No. 5,537,397, the disclosure of which is incorporated herein by reference.

Optionally, processing station 60 optionally comprises a transmitter 70 for transmitting control and data signals to DAS 50 and various subsystems (not shown) that may be mounted on rotor 36. For receiving signals transmitted by processing station 60, a receiver 72, which is connected to DAS 50 and the various subsystems of rotor 36, is mounted on the rotor. In some embodiments of the present invention, for which wireless communication between processing center 60 and rotor 36 is desired, transmission from processing station 60 to the rotor is provided by a THIM channel and transmitter 70 is a THIM transmitter and receiver 72 is a THIM receiver. In general, however, data traffic from processing station 60 to DAS 50 is substantially less than data traffic from the DAS to the processing station. As a result, control and data signal transmission from processing station 60 to rotor 36 can generally be supported, if desired, by a relatively simple wire channel between the processing station and stator 35 and a slip-ring link between the stator and rotor 36.

In accordance with some embodiments of the present invention DAS 50 codes the digital data it generates in accordance with a coding scheme and error correction algorithm known in the art. For example, in some embodiments of the present invention, DAS 50 packs the data into data packets comprising an identifying header similar to the way in which data is packed into data packets for transmission over a packet switched network. Optionally, each data packet is coded with error correction data usable to correct errors that may occur in data comprised in the data packet. DAS 50 routes the data packets so that all of each data packet is transmitted by single THIM transmitter 52.

Processor 63 uses data in the headers of the packets it receives to determine if it receives all the packets from DAS 50 that it should receive. If processor 63 determines that a frame is missing, the processor transmits a message to DAS 50 instructing the DAS to retransmit the missing packet. Similarly, if processor 63 determines that data in a packet received by processing station 60 is so badly corrupted that the data cannot be reconstituted using the error correction data included in the data packet, the processor instructs DAS 50 to resend the corrupted packet.

It is noted that error coding and packeting data generated by DAS 50 adds a "data management" overhead to the transmission of data from DAS 50 to processing station 60. Additional channel capacity that may be required to support the overhead can readily be provided by increasing the number of THIM transmitters used for transmitting data from DAS 50 to processing station 60. For example, the inventors have determined that for the sixteen slice CT-scanner described above, which generates data at a rate of 800 Mbits/sec, a data management overhead of about 300 Mbits/sec may be required to support packeting, error correction coding and retransmission of missing or corrupted packets. The total data transmission rate required by the CT-scanner becomes 1.1 Gbits/sec, which transmission data rate can be provided by adding eight THIM transmitters 52 to the twenty THIM transmitters required to transmit the 800 Mbits/sec of data without the management overhead.

Methods of configuring and transmitting the data in the data stream generated by DAS 50 for transmission by THIM transmitters other than the manner described in the preceding paragraphs will occur to person's of the art. For example, in some embodiments of the present invention, DAS 50 generates a plurality of simultaneous digital data streams from signals from X-ray detectors 32 and routes each of the data streams to a different one of the THIM transmitters. In addition it is noted that configurations of DASs, THIM transmitters and THIM receivers different from the configuration shown in FIG. 1 are possible and such different configurations will occur to a person of the art and can be advantageous. For example, the at least one THIM receiver 58 shown in FIG. 1 may comprise a plurality of THIM receivers, one for each THIM transmitter 52 or THIM receiver 58 may be located on wall 62 and coupled by wire or an ordinary radio link to processing station 60.

It should also be noted that whereas THIM transmitters 52 in FIG. 1 are shown mounted on the rotor 36, a THIM transmitter or transmitters can, in accordance with an embodiment of the present invention, advantageously be mounted on stator 35 or in the vicinity of gantry 34. For example, THIM transmitters, which are not used to transmit data from the rotor of a CT-scanner to the imager's stator may be used to provide wireless data channels from the electromagnetically noisy environment of the CT-scanner's gantry to a desired venue located at distance from the gantry. Data from the rotor to the stator may be transmitted by conventional means and from the stator to the THIM transmitter by wire. The THIM transmitter is then used to transmit the data by wireless transmission to, for example, a different room.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A CT-scanner having a gantry comprising a stator and a rotor, wherein an X-ray source and array of X-ray detectors are mounted to the rotor for determining absorption of X-rays along paths through the body of a patient imaged by the CT-scanner, the CT scanner comprising:

a processor that processes data comprised in signals generated by the X-ray detectors responsive to intensity of X-rays from the X-ray source incident on the detectors to generate an image of the patient;

at least one spread spectrum transmitter that receives data comprised in the signals generated by the X-ray detectors and transmits signals encoded with the data in accordance with a spread spectrum coding; and at least one spread spectrum receiver that receives the encoded signals transmitted by the at least one spread spectrum transmitter and forwards the encoded data to the processor.

2. A CT-scanner according to claim 1 wherein the at least one transmitter comprises at least one time hopping impulse modulation (THIM) transmitter that transmits signals encoded with the data in accordance with a THIM code and the at least one receiver comprises at least one THIM receiver that receives the encoded signals transmitted by the at least one THIM transmitter.

3. A CT-scanner according to claim 1 wherein the signals encoded with the data are free space electromagnetic waves encoded with the data.

4. A CT-scanner having a gantry comprising a stator and a rotor, wherein an X-ray source and array of X-ray detectors are mounted to the rotor for determining absorption of X-rays along paths through the body of a patient imaged by the CT-scanner, the CT scanner comprising:

a processor that processes data comprised in signals generated by the X-ray detectors responsive to intensity of X-rays from the X-ray source incident on the detectors to generate an image of the patient;

at least one transmitter that receives data comprised in the signals generated by the X-ray detectors and transmits free space electromagnetic waves encoded with the data;

at least one receiver that receives the encoded free space electromagnetic waves transmitted by the at least one transmitter and forwards the encoded data to the processor.

5. A CT-scanner according to claim 4 wherein the at least one transmitter comprises at least one spread spectrum transmitter that encodes the data in the free space electromagnetic waves in accordance with a spread spectrum code and the at least one receiver comprises at least one spread spectrum receiver.

6. A CT-scanner according to claim 5 wherein the at least one transmitter comprises at least one THIM transmitter that encodes the data in the free space electromagnetic waves in accordance with a THIM code and the at least one receiver comprises at least one THIM receiver.

7. A CT-scanner according to claim 1 or claim 4 wherein the transmitter and receiver are located in a same room.

8. A CT-scanner according to claim 1 or claim 4 wherein the transmitter is located on the gantry and the receiver is at a distance from the gantry.

9. A CT-scanner according to claim 8 wherein the transmitter and receiver are located in different rooms.

10. A CT-scanner according to claim 7 wherein the transmitter is located on the stator.

11. A CT-scanner according to claim 7 wherein the transmitter is located on the rotor.

12. A CT-scanner according to claim 1 or claim 4 wherein the transmitter is located on the rotor and the at least one receiver is located on the stator.

13. A CT-scanner according to claim 1 or claim 4 wherein the at least one receiver and the processor are near each other in a same location.

14. A CT-scanner according to claim 1 or claim 4 wherein the receiver and the processor are in different rooms.

15. A CT-scanner according to claim 1 or claim 4 wherein the at least one receiver is connected to the processor by wire over which the receiver forwards the data to the processor.

16. A CT-scanner according to claim 1 or claim 4 wherein the at least one receiver is connected to the processor by optical fiber over which the receiver forwards the data to the processor.

17. A CT-scanner according to claim 1 or claim 4 wherein the at least one transmitter comprises a plurality of transmitters.

18. A CT-scanner according to claim 17 wherein the transmitters transmit simultaneously.

19. A CT-scanner according to claim 17 wherein the at least one receiver comprises a plurality of receivers.

20. A CT-scanner according to claim 19 wherein at least two of the plurality of receivers receives transmissions from different transmitters.

21. A CT-scanner according to claim 1 or claim 4 and comprising at least one data acquisition system (DAS) mounted on the rotor connected to the X-ray detectors that receives the signals generated by the X-ray detectors and generates digital data therefrom, portions of which digital data the at least one DAS routes to each of The at least one transmitter.

22. A CT-scanner according to claim 21 wherein the at least one DAS comprises a plurality of DASs each of which acquires signals from different detectors.

23. A method of transmitting to a desired location data comprised in signals generated by X-ray detectors mounted on a rotor of a gantry comprised in a CT-scanner, the method comprising:

generating free space electromagnetic waves encoded with the data;

sensing the electromagnetic waves at the desired location; and decoding the sensed electromagnetic wave to recover the data.

24. A method according to claim 23 wherein the data is encoded in accordance with a spread spectrum code.

25. A method according to claim 24 wherein the data is encoded in accordance with a time hopping impulse modulation (THIM) code.

26. A method of transmitting to a desired location data comprised in signals generated by X-ray detectors mounted on a rotor of a gantry comprised in a CT-scanner, the method comprising:

generating signals encoded with the data in accordance with a spread spectrum code;

sensing the signals at the desired location; and decoding the sensed signals to recover the data.

27. A method according to claim 26 wherein the code is a THIM code.

28. A method according to claim 26 or claim 27 wherein the signals encoded with the data are free space electromagnetic waves encoded with the data.

* * * * *